United States Patent
Wang et al.

(10) Patent No.: US 7,158,859 B2
(45) Date of Patent: Jan. 2, 2007

(54) 5 DEGREES OF FREEDOM MOBILE ROBOT

(75) Inventors: Yulun Wang, Goleta, CA (US); Keith Phillip Laby, Santa Barbara, CA (US); Charles S. Jordan, Santa Barbara, CA (US); Steven Edward Butner, Goleta, CA (US); James Cuevas, Ventura, CA (US); Jonathan Southard, Santa Barbara, CA (US); Mike Medus, Goleta, CA (US)

(73) Assignee: InTouch Technologies, Inc., Goleta, CA (US)

( * ) Notice: Subject to any disclaimer, the term of this patent is extended or adjusted under 35 U.S.C. 154(b) by 263 days.

(21) Appl. No.: 10/439,122

(22) Filed: May 14, 2003

(65) Prior Publication Data

US 2004/0138547 A1 Jul. 15, 2004

Related U.S. Application Data (60) Provisional application No. 60/440,586, filed on Jan. 15, 2003.

(51) Int. Cl.
*G06F 19/00* (2006.01)

(52) U.S. Cl. .................. 700/245; 700/247; 700/248; 700/251; 700/257; 700/258; 700/259; 700/260; 700/261; 700/262; 700/264; 318/568.11; 318/568.12; 318/568.13; 318/568.16; 318/568.21; 318/568.25; 606/1; 606/102; 606/130; 606/139; 600/117; 600/118; 600/407; 600/426; 600/429; 600/587; 600/595; 901/1; 901/2; 901/27

(58) Field of Classification Search ........ 700/131–132, 700/245–248, 251, 253, 257–262, 264; 606/1, 606/102, 130, 139; 318/568.11, 568.12, 318/568.13, 568.16, 568.21, 568.22, 568.25; 600/102–103, 109, 117–118, 407, 426, 429, 600/587, 595; 901/1–2, 27, 36
See application file for complete search history.

(56) References Cited

U.S. PATENT DOCUMENTS 5,374,879 A 12/1994 Pin et al.

(Continued)

FOREIGN PATENT DOCUMENTS

CA 2289697 A1 11/1998

OTHER PUBLICATIONS

Mack, Minimally invasive and robotic surgery, 2001, IEEE, pp. 568-572.*

(Continued)

*Primary Examiner*—Thomas Black
*Assistant Examiner*—McDieunel Marc
(74) *Attorney, Agent, or Firm*—Ben J. Yorks; Irell & Manella LLP (57) ABSTRACT

A robotic system that includes a remote controlled robot with at least five degrees of freedom and a teleconferencing function. The robot may include a camera, a monitor and a holonomic platform all attached to a robot housing. The robot may be controlled by a remote control station that also has a camera and a monitor. The remote control station may be linked to a base station that is wirelessly coupled to the robot. The cameras and monitors allow a care giver at the remote location to monitor and care for a patient through the robot. The holonomic platform provides three degrees of freedom to allow the robot to move about a home or facility to locate and/or follow a patient. The robot also has mechanisms to provide at least two degrees of freedom for the camera.

46 Claims, 9 Drawing Sheets

U.S. PATENT DOCUMENTS

| | | | | |
|---|---|---|---|---|
| 5,802,494 | A | * | 9/1998 | Kuno ............................. 705/2 |
| 5,959,423 | A | | 9/1999 | Nakanishi et al. |
| 6,259,806 | B1 | | 7/2001 | Green |
| 6,292,713 | B1 | | 9/2001 | Jouppi et al. |
| 6,346,950 | B1 | | 2/2002 | Jouppi |
| 6,369,847 | B1 | | 4/2002 | James et al. |
| 6,430,471 | B1 | | 8/2002 | Kintou et al. |
| 6,438,457 | B1 | * | 8/2002 | Yokoo et al. ................ 700/245 |
| 6,463,361 | B1 | | 10/2002 | Wang et al. |
| 6,491,701 | B1 | | 12/2002 | Tierney et al. |
| 6,496,099 | B1 | | 12/2002 | Wang et al. |
| 6,522,906 | B1 | * | 2/2003 | Salisbury et al. ........... 600/407 |
| 6,535,793 | B1 | | 3/2003 | Allard |
| 6,549,215 | B1 | | 4/2003 | Jouppi |
| 6,587,750 | B1 | * | 7/2003 | Gerbi et al. ................. 700/245 |
| 6,594,552 | B1 | * | 7/2003 | Nowlin et al. .............. 700/260 |
| 6,684,129 | B1 | * | 1/2004 | Salisbury et al. ........... 700/245 |
| 6,799,065 | B1 | * | 9/2004 | Niemeyer ................... 600/407 |
| 6,839,612 | B1 | * | 1/2005 | Sanchez et al. ............. 700/245 |
| 6,852,107 | B1 | * | 2/2005 | Wang et al. .................... 606/1 |
| 6,995,664 | B1 | | 2/2006 | Darling |
| 2001/0054071 | A1 | | 12/2001 | Loeb |
| 2002/0027597 | A1 | | 3/2002 | Sachau |
| 2002/0057279 | A1 | | 5/2002 | Jouppi |
| 2002/0058929 | A1 | | 5/2002 | Green |
| 2002/0063726 | A1 | | 5/2002 | Jouppi |
| 2002/0120362 | A1 | | 8/2002 | Lathan et al. |
| 2002/0130950 | A1 | | 9/2002 | James et al. |
| 2002/0141595 | A1 | | 10/2002 | Jouppi |
| 2002/0183894 | A1 | | 12/2002 | Wang et al. |
| 2003/0050733 | A1 | | 3/2003 | Wang et al. |
| 2003/0114962 | A1 | * | 6/2003 | Niemeyer ................... 700/245 |
| 2003/0135203 | A1 | * | 7/2003 | Wang et al. .................... 606/1 |
| 2003/0144649 | A1 | * | 7/2003 | Ghodoussi et al. ............. 606/1 |
| 2003/0220541 | A1 | * | 11/2003 | Salisbury et al. ........... 600/101 |
| 2005/0038416 | A1 | * | 2/2005 | Wang et al. .................... 606/1 |

OTHER PUBLICATIONS

Davies, Robotics in minimilly invasive surgery, 1995, Internet, pp. 5/1-5/2.*

Stoianovici et al., Robotic tools for minimally invasive urologic surgery, 2002, Internet, 1-17.*

Tendick et al., Human-machine interfaces for minimally invasive sugery, 1997, IEEE, pp. 1-6.*

Schaaf, Robotic surgery: The future in now, 2001, Internet, pp. 1-11.*

Student BMJ, Robotics in surgery, 2002, Internret, pp. 1-4.*

Stephenson, Dr. robot tested at Hokins, 2003, Internet, p. 1-2.*

CNN.com/Technology, Paging R. Robot: Machine helps doctors with patients, 2003, Internet, 1-3.*

Roland Piquepaille's Technology Trens, How new technologies are modifying your way of life, 2003, Internet, p. 1-2.*

Paulos et al., "A World Wide Web Telerobotic Remote Environment Browser", http://vive.cs.berkeley.edu/capek, 1995.

Telepresence Research, Inc., "Telepresence Mobile Robot System", http://www.telepresence.com/telepresence-research/TELEROBOT/, Feb. 20, 1995.

Zorn, Benjamin G., "Ubiquitos Telepresence", http://www.cs.colorado.edu/~zorn/ut/vision.html, Mar. 5, 1996.

Paulos, et al., "Ubiquitos Tele-embodiment: Applications and Implications", International Journal of Human Computer Studies, Jun. 1997, vol. 46, No. 6, pp. 861-877.

Paulos, et al., "Designing Personal Tele-Embodiment", Presented at the IEEE International Conference on Robotics and Animation, Leuven, Belgium, May 20, 1998.

Harmo et al., "Moving Eye—Interactive Telepresence Over Internet With a Ball Shaped Mobile Robot", 2000.

Loeb, Gerald, "Virtual Visit: Improving Communication for Those Who Need It Most", 2001.

Paulos, Eric John, "Personal Tele-Embodiment", 2001.

Hees, William P., "Communications Design for a Remote Presence Robot", Jan. 14, 2002.

Jacobs et al., "TeleRehab: Applying Telemedicine to Outpatient Physical Therapy", 2002.

Jouppi, et al., :Mutually-Immersive Audio Telepresence, Audio Engineering Society Convention Paper, presented at 113$^{th}$ Convention Oct. 2002.

Jouppi, Norman P., "First Steps Towards Mutually-Immersive Mobile Telepresence", 2002.

Eillison et al., "Telerounding and Patient Satisfaction Following Surgery".

* cited by examiner

5 DEGREES OF FREEDOM MOBILE ROBOT

REFERENCE TO CROSS-RELATED APPLICATIONS

This application claims priority to Provisional Application No. 60/440,586 filed on Jan. 15, 2003.

BACKGROUND OF THE INVENTION

1. Field of the Invention

The subject matter disclosed generally relates to the use of robotics in the field of healthcare.

2. Background Information

There is a growing need to provide remote health care to patients that have a variety of ailments ranging from Alzheimers to stress disorders. To minimize costs it is desirable to provide home care for such patients. Home care typically requires a periodic visit by a health care provider such as a nurse or some type of assistant. Due to financial and/or staffing issues the health care provider may not be there when the patient needs some type of assistance. Additionally, existing staff must be continuously trained, which can create a burden on training personnel. It would be desirable to provide a system that would allow a health care provider to remotely care for a patient without being physically present.

Robots have been used in a variety of applications ranging from remote control of hazardous material to assisting in the performance of surgery. For example, U.S. Pat. No. 5,762,458 issued to Wang et al. discloses a system that allows a surgeon to perform minimally invasive medical procedures through the use of robotically controlled instruments. One of the robotic arms in the Wang system moves an endoscope which has a camera that allows a surgeon to view a surgical area of a patient.

Tele-robots such as hazardous waste handlers and bomb detectors may contain a camera that allows the operator to view the remote site. Canadian Pat. No. 2289697 issued to Treviranus, et al. discloses a teleconferencing platform that has both a camera and a monitor. The Treviranus patent also discloses embodiments with a mobile platform and different mechanisms for moving the camera and the monitor.

BRIEF SUMMARY OF THE INVENTION

A robot that may include a three degree of freedom platform coupled to a housing. The robot further has a monitor and a camera coupled to the housing. A first device of the robot moves the camera in a fourth degree of freedom. A second device of the robot moves the camera in a second degree of freedom.

DETAILED DESCRIPTION

Disclosed is a robotic system that includes a remote controlled robot with at least five degrees of freedom and a teleconferencing function. The robot may include a camera, a monitor and a holonomic platform all attached to a robot housing. The robot may be controlled by a remote control station that also has a camera and a monitor. The remote control station may be linked to a base station that is wirelessly coupled to the robot. The cameras and monitors allow a care giver at the remote location to monitor and care for a patient through the robot. The holonomic platform provides three degrees of freedom to allow the robot to move about a home or facility to locate and/or follow a patient. The robot also has mechanisms to provide at least two degrees of freedom for the camera.

Figure 1:
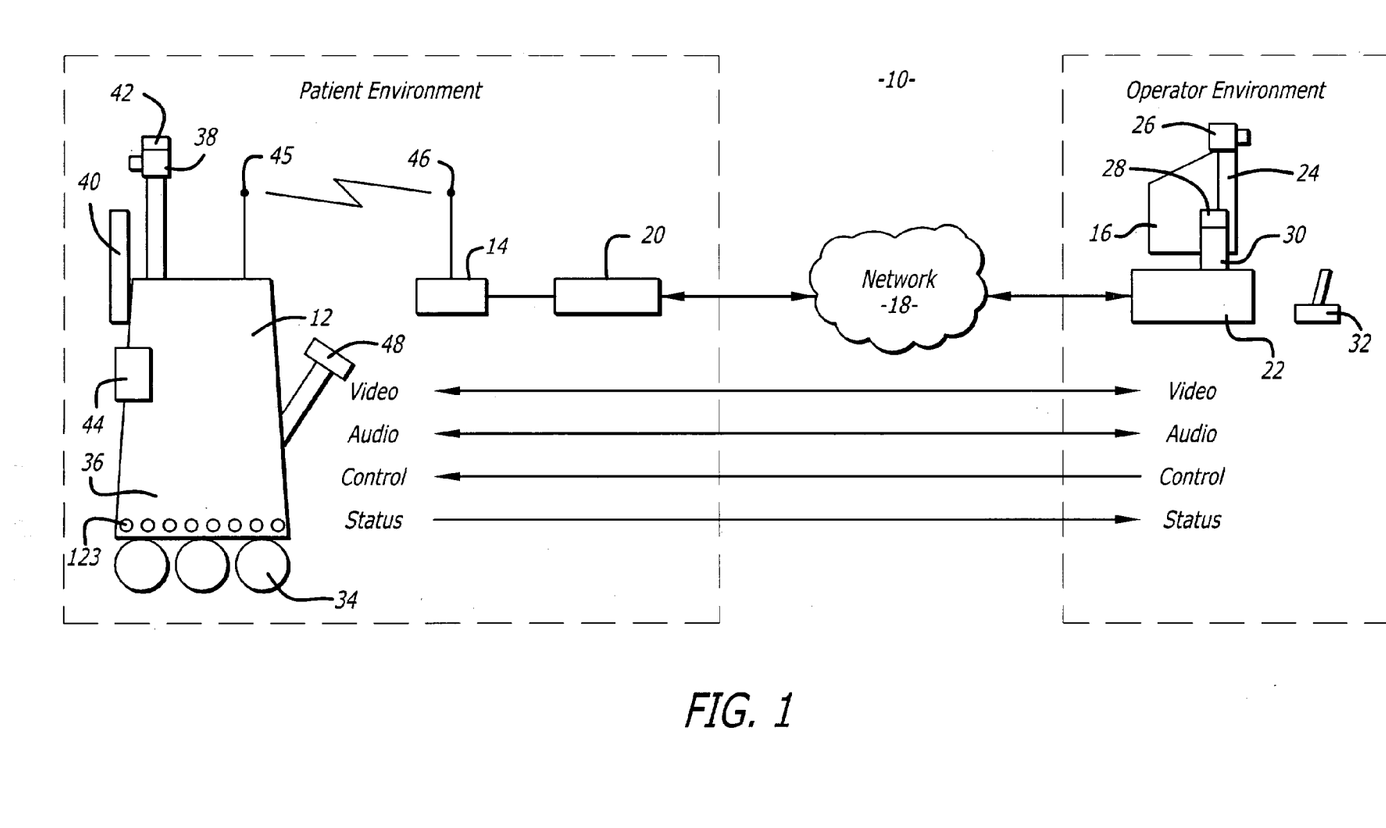
FIG. 1 is an illustration of a robotic system.

Referring to the drawings more particularly by reference numbers, FIG. 1 shows a robotic system 10. The robotic system 10 includes a robot 12, a base station 14 and a remote control station 16. The remote control station 16 may be coupled to the base station 14 through a network 18. By way of example, the network 18 may be either a packet switched network such as the Internet, or a circuit switched network such has a Public Switched Telephone Network (PSTN) or other broadband system. The base station 14 may be coupled to the network 18 by a modem 20 or other broadband network interface device.

The remote control station 16 may include a computer 22 that has a monitor 24, a camera 26, a microphone 28 and a speaker 30. The computer 22 may also contain an input device 32 such as a joystick or a mouse. The control station 16 is typically located in a place that is remote from the robot 12. Although only one remote control station 16 is shown, the system 10 may include a plurality of remote stations. Additionally, although only one robot 12 is shown, it is to be understood that the system 10 may have a plurality of robots 12. In general any number of robots 12 may be controlled by any number of remote stations 16. For example, one remote station 16 may be coupled to a plurality of robots 12, or one robot 12 may be coupled to a plurality of remote stations 16.

The robot 12 includes a movement platform 34 that is attached to a robot housing 36. Also attached to the robot housing 36 are a camera 38, a monitor 40, a microphone(s) 42 and a speaker 44. The microphone 42 and speaker 30 may create a stereophonic sound. The robot 12 may also have an antenna 45 that is wirelessly coupled to an antenna 46 of the base station 14. The system 10 allows a user at the remote control station 16 to move the robot 12 through the input device 32. The robot camera 38 is coupled to the remote monitor 24 so that a user at the remote station 16 can view a patient. Likewise, the robot monitor 40 is coupled to the remote camera 26 so that the patient can view the user. The microphones 28 and 42, and speakers 30 and 44, allow for audible communication between the patient and the user. The robot 12 may further have a handle 48 that can be rotated to a down position to allow someone to manually push or pull the robot 12.

The remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

Figure 2:
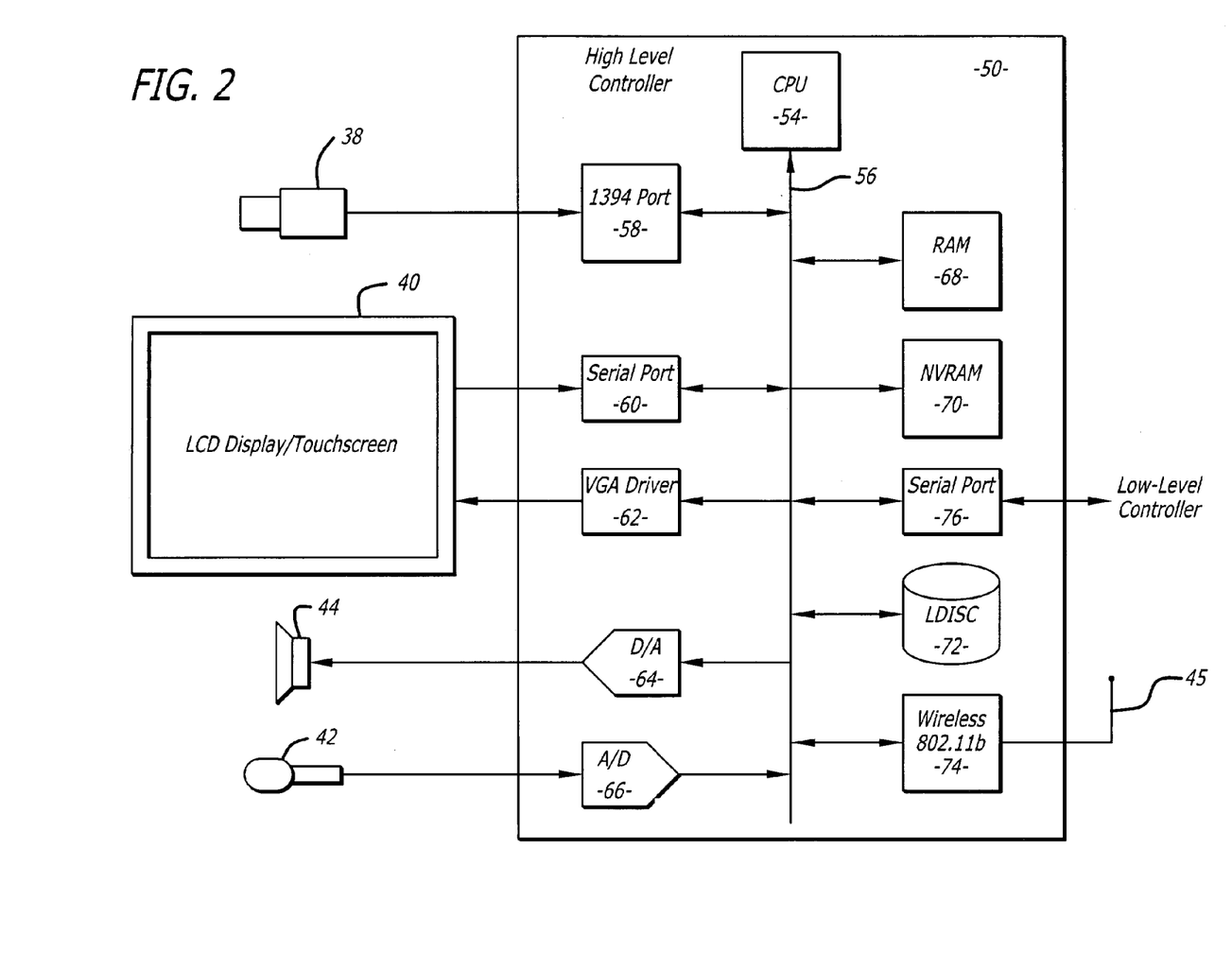
FIG. 2 is a schematic of an electrical system of a robot.
Figure 3:
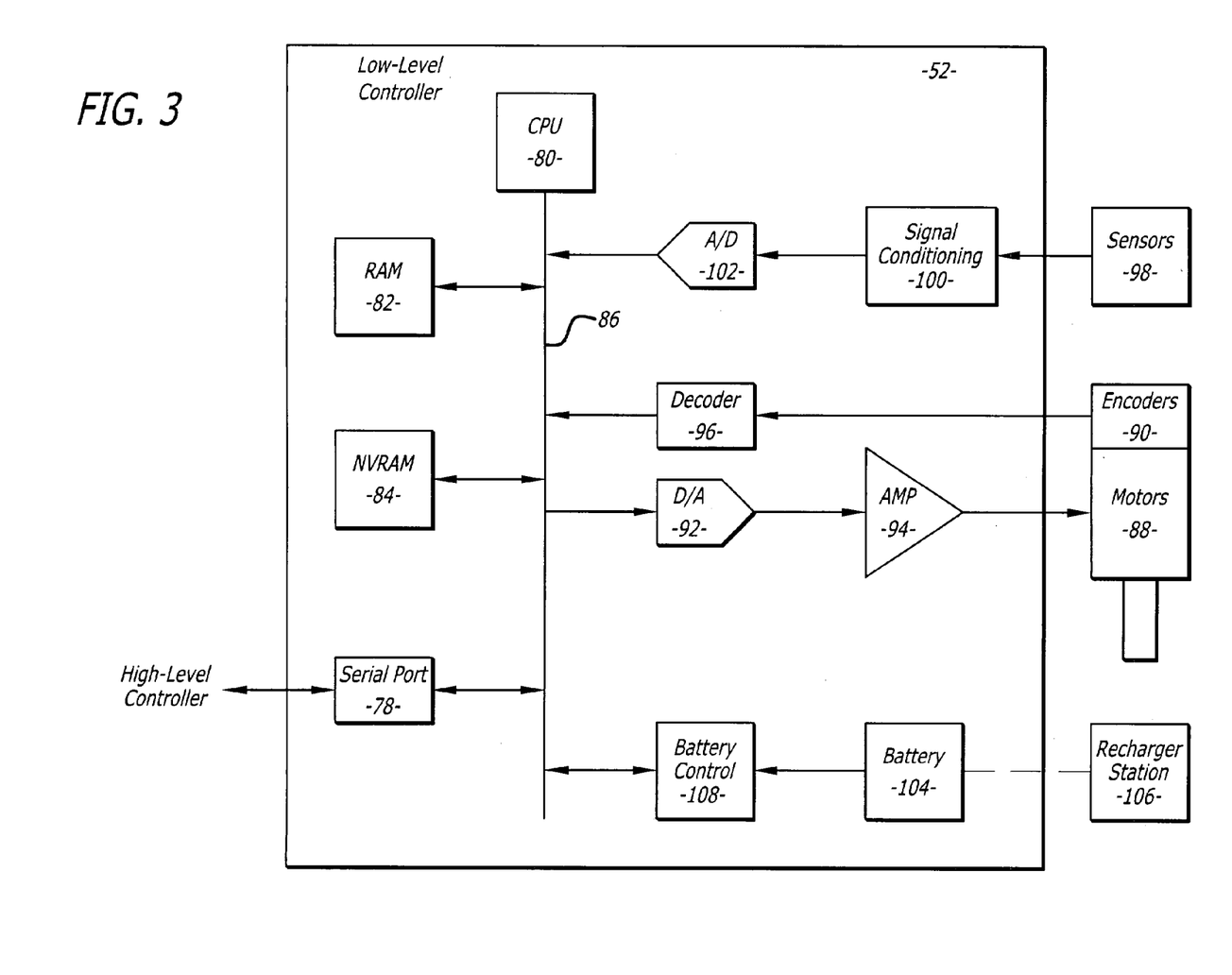
FIG. 3 is a further schematic of the electrical system of the robot.

FIGS. 2 and 3 show an embodiment of the robot 12. The robot 12 may include a high level control system 50 and a low level control system 52. The high level control system 50 may include a processor 54 that is connected to a bus 56. The bus 56 is coupled to the camera 38 by an input/output (I/O) port 58, and to the monitor 40 by a serial output port 60 and a VGA driver 62. The monitor 40 may include a touchscreen function that allows the patient to enter input by touching the monitor screen.

The speaker 44 is coupled to the bus 56 by a digital to analog converter 64. The microphone 42 is coupled to the bus 56 by an analog to digital converter 66. The high level controller 50 may also contain random access memory (RAM) device 68, a non-volatile RAM device 70 and a mass storage device 72 that are all coupled to the bus 56. The mass storage device 72 may contain medical files of the patient that can be accessed by the user at the remote control station 16. For example, the mass storage device 72 may contain a picture of the patient. The user, particularly a health care provider, can recall the old picture and make a side by side comparison on the monitor 24 with a present video image of the patient provided by the camera 38. The robot antennae 45 may be coupled to a wireless transceiver 74. By way of example, the transceiver 74 may transmit and receive information in accordance with IEEE 802.11b.

The controller 54 may operate with a LINUX OS operating system. The controller 54 may also operate MS WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 50 operates to control the communication between the robot 12 and the remote control station 16.

The high level controller 50 may be linked to the low level controller 52 by serial ports 76 and 78. The low level controller 52 includes a processor 80 that is coupled to a RAM device 82 and non-volatile RAM device 84 by a bus 86. The robot 12 contains a plurality of motors 88 and motor encoders 90. The encoders 90 provide feedback information regarding the output of the motors 88. The motors 88 can be coupled to the bus 86 by a digital to analog converter 92 and a driver amplifier 94. The encoders 90 can be coupled to the bus 86 by a decoder 96. The robot 12 also has a number of proximity sensors 98 (see also FIG. 1). The position sensors 98 can be coupled to the bus 86 by a signal conditioning circuit 100 and an analog to digital converter 102.

The low level controller 52 runs software routines that mechanically actuate the robot 12. For example, the low level controller 52 provides instructions to actuate the movement platform to move the robot 12. The low level controller 52 may receive movement instructions from the high level controller 50. The movement instructions may be received as movement commands from the remote control station. Although two controllers are shown, it is to be understood that the robot 12 may have one controller controlling the high and low level functions.

The various electrical devices of the robot 12 may be powered by a battery(ies) 104. The battery 104 may be recharged by a battery recharger station 106. The low level controller 52 may include a battery control circuit 108 that senses the power level of the battery 104. The low level controller 52 can sense when the power falls below a threshold and then send a message to the high level controller 50. The high level controller 50 may include a power management software routine that causes the robot 12 to move so that the battery 104 is coupled to the recharger 106 when the battery power falls below a threshold value. Alternatively, the user can direct the robot 12 to the battery recharger 106. Additionally, the battery 104 may be replaced or the robot 12 may be coupled to a wall power outlet by an electrical cord (not shown).

Figure 4:
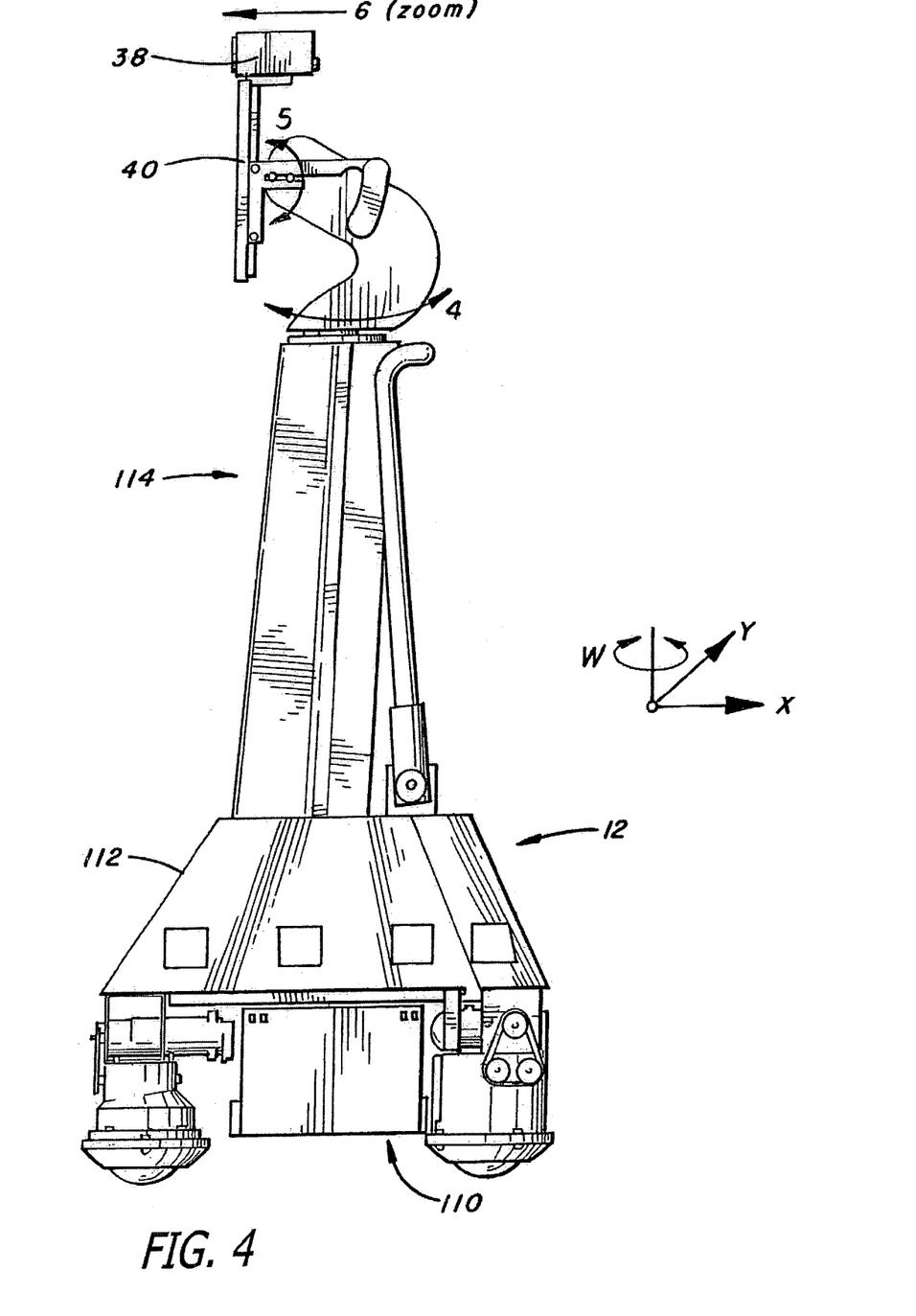
FIG. 4 is side view of the robot.

FIG. 4 shows an embodiment of the robot 12. The robot 12 may include a holonomic platform 110 that is attached to a robot housing 112. The holonomic platform 110 provides three degrees of freedom to allow the robot 12 to move in any direction.

The robot 12 may have a pedestal assembly 114 that supports the camera 38 and the monitor 40. The pedestal assembly 114 may have two degrees of freedom so that the camera 26 and monitor 24 can be swiveled and pivoted as indicated by the arrows.

Figure 5:
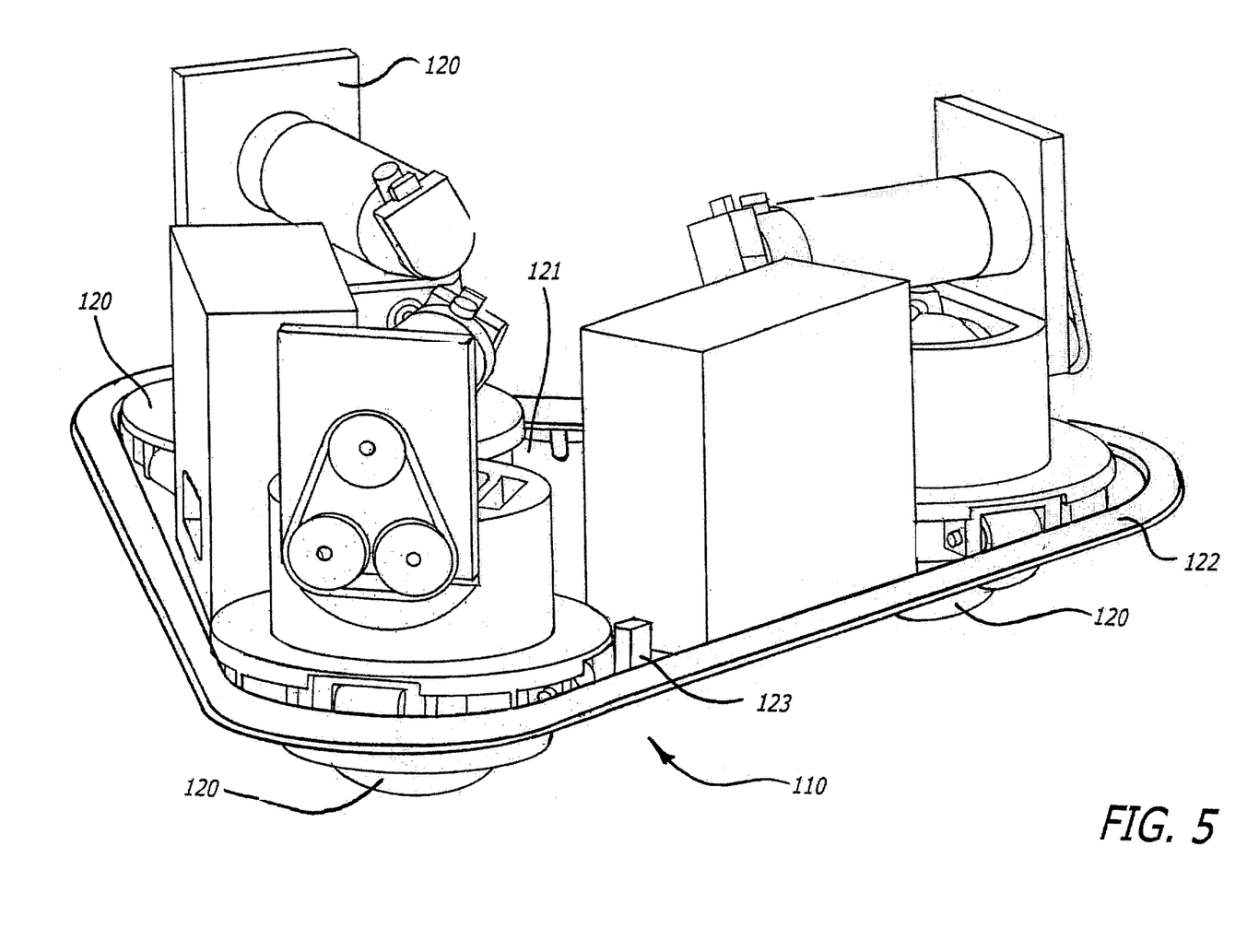
FIG. 5 is a top perspective view of a holonomic platform of the robot.

As shown in FIG. 5 the holonomic platform 110 may include three roller assemblies 120 that are mounted to a base plate 121. The roller assemblies 120 allow for movement in any direction.

The robot housing 112 may include a bumper 122. The bumper 122 may be coupled to optical position sensors 123 that detect when the bumper 122 has engaged an object. After engagement with the object the robot can determine the direction of contact and prevent further movement into the object.

Figure 6:
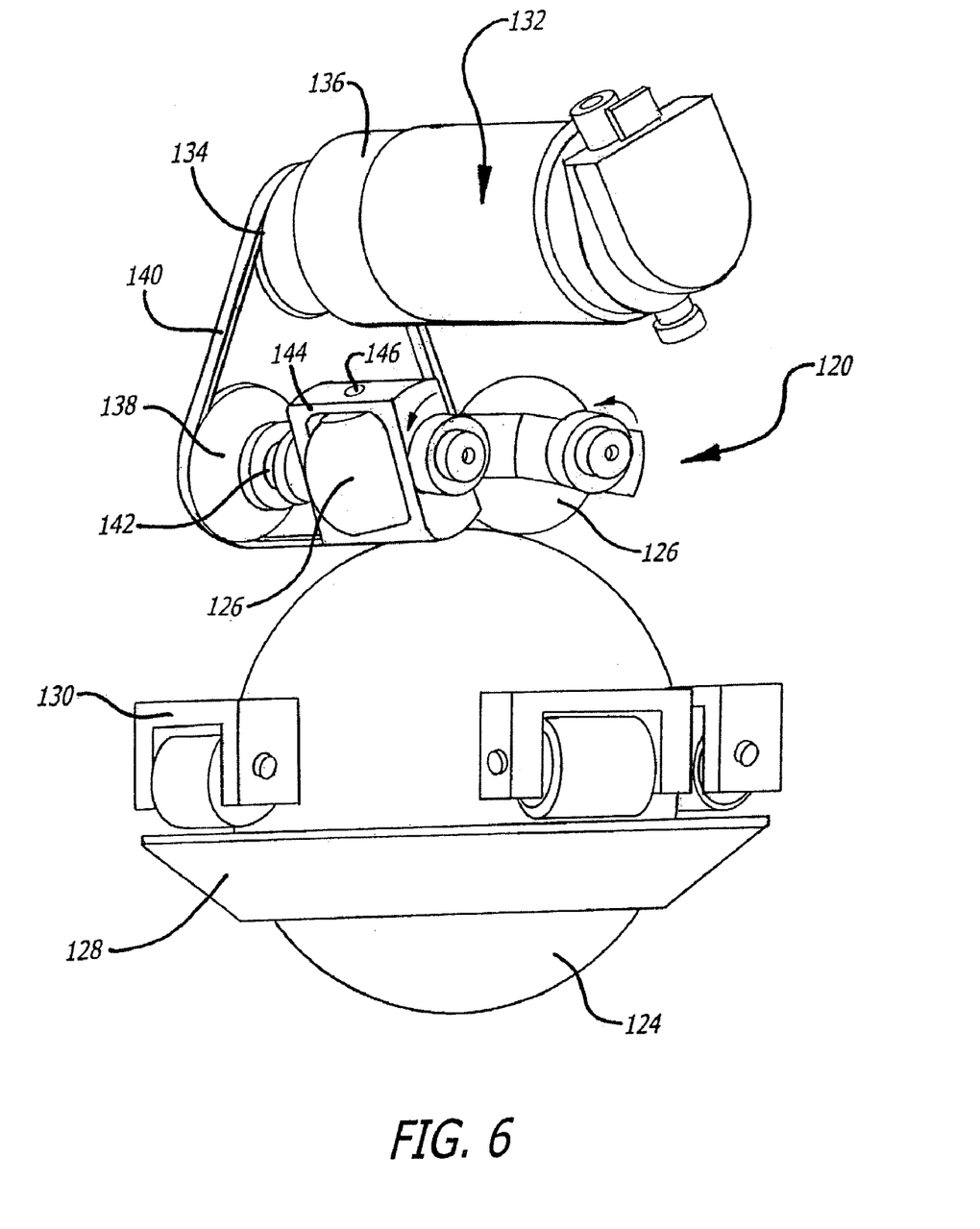
FIG. 6 is a side perspective view of a roller assembly of the holonomic platform.

FIG. 6 shows an embodiment of a roller assembly 120. Each assembly 120 may include a drive ball 124 that is driven by a pair of transmission rollers 126. The assembly 120 includes a retainer ring 128 and a plurality of bushings 130 that allow the ball 124 to rotate but prevent movement in a z direction.

The transmission rollers 126 are coupled to a motor assembly 132. The assembly 132 corresponds to the motor 88 shown in FIG. 3. The motor assembly 132 includes an output pulley 134 attached to a motor 136. The output pulley 134 is coupled to a pair of ball pulleys 138 by a drive belt 140. The ball pulleys 138 are attached to drive pins 142 that are attached to a transmission bracket 144. The transmission rollers 126 are attached to a transmission bracket 144 by a roller pin 146.

Rotation of the output pulley 134 rotates the ball pulleys 138. Rotation of the ball pulleys 138 cause the transmission rollers 126 to rotate and spin the ball 124 through frictional forces. Spinning the ball 124 will move the robot 12. The drive balls 126 are out of phase so that one of the balls 126 is always in contact with ball 124. The roller pin 146 and bracket 144 allow the transmission rollers 126 to freely spin and allow orthogonal directional passive movement when one of the other roller assemblies 120 is driving and moving the robot 12.

Figure 7:
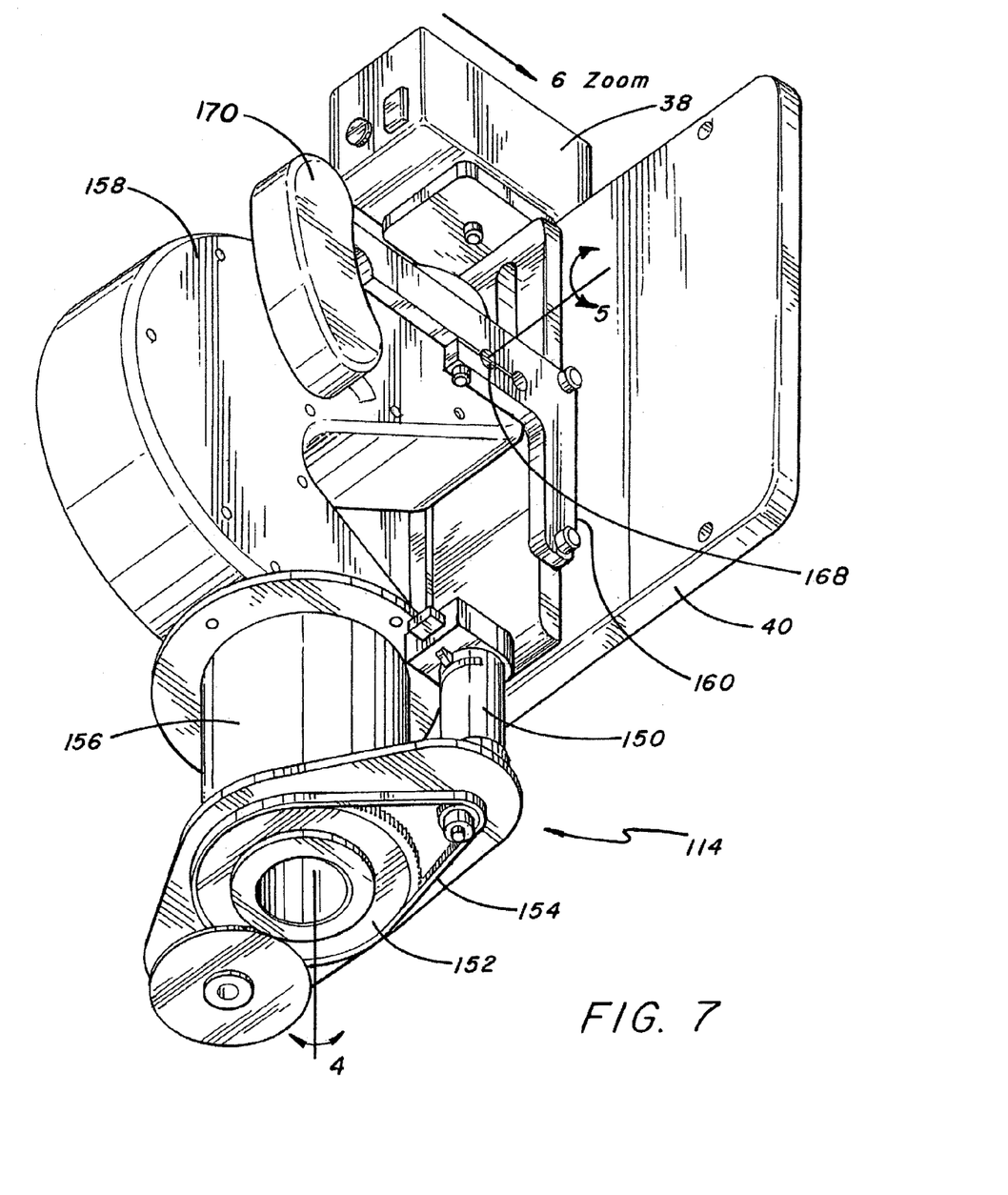
FIG. 7 is a bottom perspective view showing a pedestal assembly of the robot.

As shown in FIG. 7, the pedestal assembly 114 may include a motor 150 that is coupled to a gear 152 by a belt 154. The gear 152 is attached to a bushing 156. The bushing 156 is attached to an arm 158 that is coupled to the camera 38 and monitor 40 by a bracket 160. Activation of the motor 150 rotates the gear 152 and causes the camera 38 and monitor 40 to spin about a spin axis (see also FIG. 4) as indicated by the arrows 4. The motor 150 provides a fourth degree of freedom for the camera 38 and the monitor 40.

Figure 8:
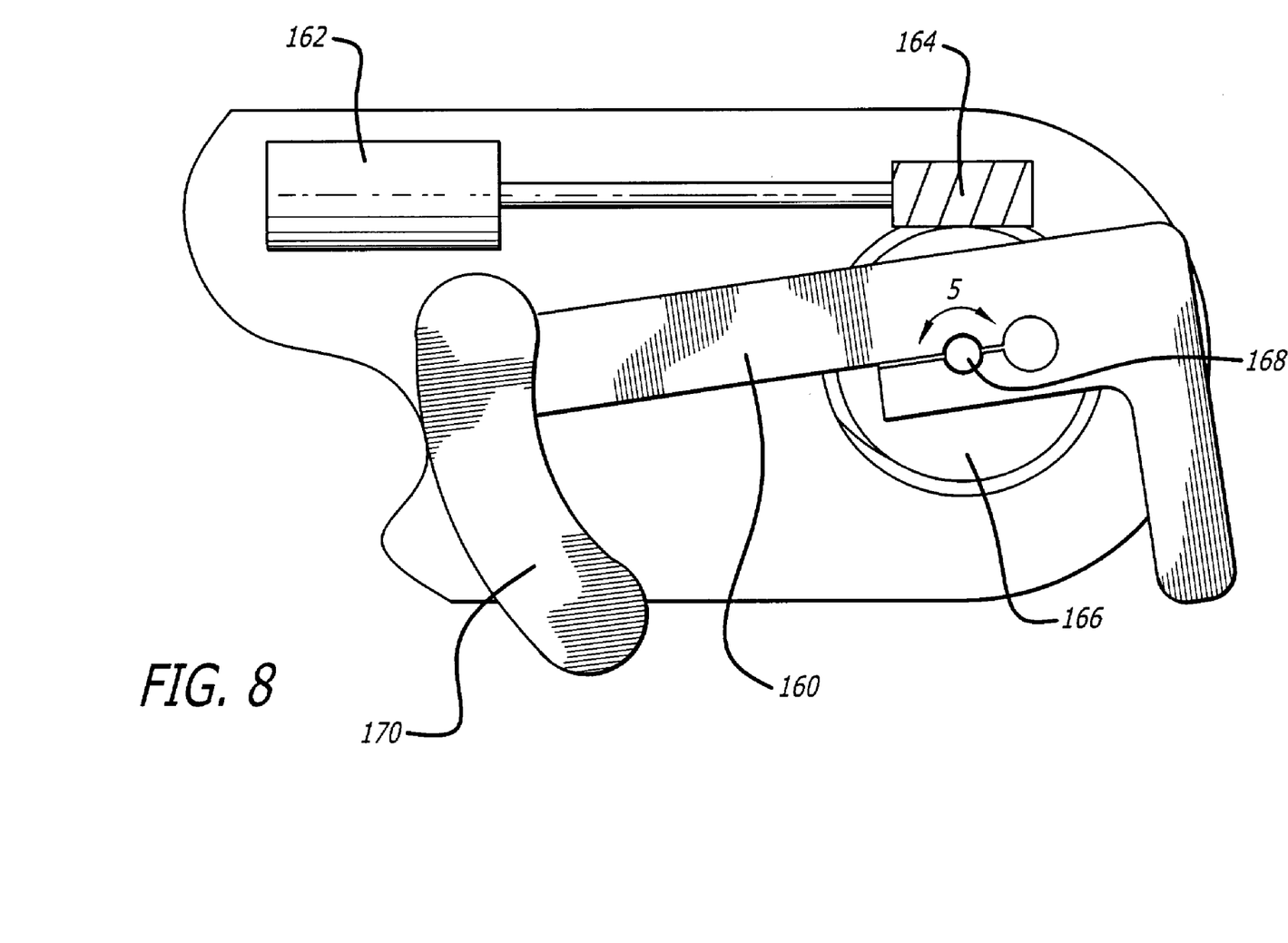
FIG. 8 is a sectional view showing an actuator of the pedestal assembly.

As shown in FIG. 8, the assembly 114 may further include a tilt motor 162 within the arm 158 that can cause the monitor 40 and camera 38 to pivot about a pivot axis as indicated by the arrows 5 (see also FIGS. 4 and 7). The pivot axis may intersect the spin axis so that the assembly 114 functions like a neck that can turn the camera 38 side to side, and up and down.

The tilt motor 162 may rotate a worm 164 that rotates a worm gear 166. The pin 168 is rigidly attached to both the worm gear 166 and the bracket 160 so that rotation of the gear 166 pivots the camera 38 and the monitor 40. The bracket 160 may have a counterweight 170 to counter the weight of the camera 38 and monitor 40. The camera 38 may also include a zoom feature to provide yet another degree of freedom for the operator. The motor 162 provides a fifth degree of freedom for the camera 38 and the monitor 40. Although motors 150 and 162 are shown and described, it is to be understood that other actuators could be implemented into the robot 12.

Figure 9:
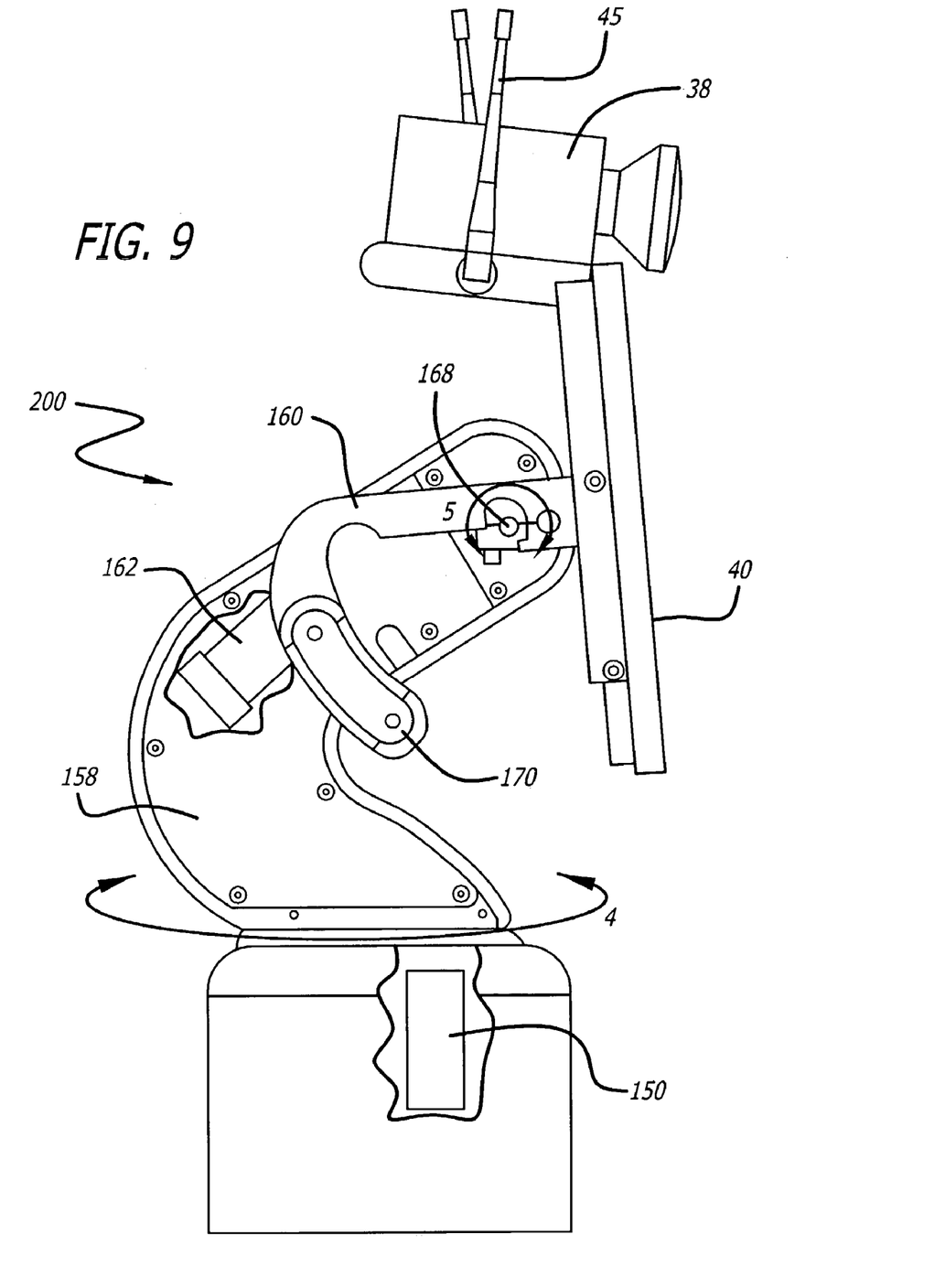
FIG. 9 is a side view of a robot head.

FIG. 9 shows a robot head 200 that can both pivot and spin the camera 38 and the monitor 40. The robot head 200 can be similar to the robot 12 but without the platform 110. The robot head 200 may have the same mechanisms and parts to both pivot the camera 38 and monitor 40 about the pivot axis 4, and spin the camera 38 and monitor 40 about the spin axis 5. The pivot axis may intersect the spin axis. Having a robot head 200 that both pivots and spins provides a wide viewing area.

In operation, the robot 12 or robot head may be placed in a home or a facility where one or more patients are to be monitored and/or assisted. The facility may be a hospital or a residential care facility. By way of example, the robot 12 may be placed in a home where a health care provider may monitor and/or assist the patient. Likewise, a friend or family member may communicate with the patient. The cameras and monitors at both the robot/robot head and remote control station allow for teleconferencing between the patient and the person at the remote station.

The robot 12 can be maneuvered through the home or facility by manipulating the input device 32 at the remote station 16.

The five degrees of freedom in the robot 12 allow the operator at the remote station 16 to obtain any desired viewing angle. The robot 12 may have autonomous movement. For example, the robot 12 may be programmed to automatically move to a patients room at a certain time to dispense drugs located in a drawer (not shown) without input from the remote station 16. The robot 12 can be programmed to monitor and/or assist a patient 24 hours a day, 7 days a week. Such a monitoring capability is enhanced by the autonomous recharging function of the robot.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A robot, comprising:
   a housing;
   a mobile platform that is attached to said housing and has three degrees of freedom;
   a camera coupled to said housing;
   a monitor mechanically coupled to said camera to move with said camera;
   a first device that moves said camera and said monitor in a fourth degree of freedom; and,
   a second device that moves said camera and said monitor in a fifth degree of freedom.

2. The robot of claim 1, wherein said platform is a holonomic platform.

3. The robot of claim 1, wherein said camera and said monitor pivots about a pivot axis.

4. The robot of claim 1, wherein said camera and said monitor spins about a spin axis.

5. The robot of claim 1, wherein the pivot axis intersects the spin axis.

6. The robot of claim 1, further comprising a wireless transceiver coupled to said housing.

7. The robot of claim 1, wherein said first and second devices each include an electric motor.

8. A robot, comprising:
   a housing;
   a mobile platform that is attached to said housing and has three degrees of freedom;
   a camera coupled to said housing;
   a monitor mechanically coupled to said camera to move with said camera;
   first movement means for moving said camera and said monitor in a fourth degree of freedom; and,
   second movement means for moving said camera.and said monitor in a fifth degree of freedom.

9. The robot of claim 8, wherein said platform is a holonomic platform.

10. The robot of claim 8, wherein said camera and said monitor pivots about a pivot axis.

11. The robot of claim 8, wherein said camera and said monitor spins about a spin axis.

12. The robot of claim 8, wherein the pivot axis intersects the spin axis.

13. The robot of claim 8, further comprising a wireless transceiver coupled to said housing.

14. The robot of claim 8, wherein said first and second movement means each include an electric motor.

15. A robot, comprising:
    a housing;
    a mobile platform that is attached to said housing and has three degrees of freedom;
    a camera coupled to said housing so that said camera can pivot about a pivot axis and spin about a spin axis;
    a monitor mechanically coupled to said camera to move with said camera;
    a first actuator coupled to said housing, said camera and said monitor; and,
    a second actuator coupled to said housing, said camera and said monitor.

16. The robot of claim 15, wherein said first actuator is an electric motor.

17. The robot of claim 15, wherein said second actuator is an electric motor.

18. The robot of claim 15, wherein said platform is a holonomic platform.

19. The robot of claim 15, wherein the pivot axis intersects the spin axis.

20. The robot of claim 15, further comprising a wireless transceiver coupled to said housing.

21. The robot of claim 15, wherein said first and second actuators are coupled to said monitor.

22. A method for operating a robot, comprising:
    moving a robot along a surface in three degrees of freedom, the robot having a camera that is mechanically coupled to and moves with a monitor;
    moving the camera and the monitor of the robot in a fourth degree of freedom; and,
    moving the camera and the monitor in a fifth degree of freedom of the robot.

23. The method of claim 22, wherein the fourth degree of freedom is pivoting the camera and the monitor about a pivot axis and the fifth degree of freedom is spinning the camera and the monitor about a spin axis.

24. The method of claim 22, further comprising wirelessly transmitting instructions to the robot.

25. A robotic system, comprising:
a remote station; and,
a robot coupled to said remote station, said robot including a mobile platform that has three degrees of freedom and a camera, and a monitor mechanically coupled to said camera to move with said camera, said camera and said monitor can move in a fourth degree of freedom and a fifth degree of freedom.

26. The robot system of claim 25, wherein said remote station includes a computer.

27. The robot system of claim 26, wherein said remote station includes an input device.

28. The robot system of claim 25, wherein said robot includes a wireless transceiver.

29. The robot system of claim 28, further comprising a base station coupled to said wireless transceiver and said remote station.

30. A robot head, comprising:
a housing;
a camera coupled to said housing so that said camera can pivot about a pivot axis and spin about a spin axis;
a monitor mechanically coupled to said camera to move with said camera;
a first actuator coupled to said housing, said camera and said monitor; and,
a second actuator coupled to said housing, said camera and said monitor.

31. The robot head of claim 30, wherein said first actuator is an electric motor.

32. The robot head of claim 30, wherein said second actuator is an electric motor.

33. The robot head of claim 30, wherein the pivot axis intersects the spin axis.

34. The robot head of claim 30, further comprising a wireless transceiver coupled to said housing.

35. A robot head, comprising:
a housing;
a camera coupled to said housing;
a monitor mechanically coupled to said camera to move with said camera;
first movement means for pivoting said camera and said monitor about a pivot axis; and,
second movement means for spinning said camera and said monitor about a spin axis.

36. The robot head of claim 35, wherein the pivot axis intersects the spin axis.

37. The robot head of claim 35, further comprising a wireless transceiver coupled to said housing.

38. The robot head of claim 35, wherein said first and second movements means include an electric motor.

39. A method for operating a robot head, comprising:
pivoting together a camera and a monitor of a robot head about a pivot axis, the monitor being mechanically coupled to the camera to move with the camera; and,
spinning the camera and a monitor of the robot head about a spin axis.

40. The method of claim 39, further comprising pivoting and spinning the monitor.

41. The method of claim 39, further comprising wirelessly transmitting instructions to the robot.

42. A robotic system, comprising:
a remote station; and,
a robot head coupled to said remote station, said robot head including a camera and a monitor mechanically coupled to said camera to rotate with said camera, said camera and said monitor can pivot together about a pivot axis and spin about a spin axis.

43. The robot system of claim 42, wherein said remote station includes a computer.

44. The robot system of claim 43, wherein said remote station includes an input device.

45. The robot system of claim 42, wherein said robot head includes a wireless transceiver.

46. The robot system of claim 45, further comprising a base station coupled to said wireless transceiver and said remote station.

* * * * *